(12) United States Patent
Kandil (10) Patent No.: US 7,722,906 B2
(45) Date of Patent: *May 25, 2010

(54) **POLYUNSATURATED FATTY ACID FRACTIONS OF *NIGELLA SATIVA* L. SEEDS**

(75) Inventor: Osama Kandil, Cairo (EG)

(73) Assignee: Biopharm Research & Development Corporation Limited (GB)

( * ) Notice: Subject to any disclaimer, the term of this patent is extended or adjusted under 35 U.S.C. 154(b) by 1327 days.

This patent is subject to a terminal disclaimer.

(21) Appl. No.: 10/809,869

(22) Filed: Mar. 26, 2004

(65) Prior Publication Data

US 2005/0214241 A1    Sep. 29, 2005

(51) Int. Cl.
*A61K 36/00* (2006.01)
*A61K 36/28* (2006.01)
*A61K 8/02* (2006.01)

(52) U.S. Cl. .................. 424/776; 424/764; 424/401; 514/885

(58) Field of Classification Search .......... 424/764, 424/401; 514/885
See application file for complete search history.

(56) References Cited

U.S. PATENT DOCUMENTS

| | | | |
|---|---|---|---|
| 5,041,439 | A | 8/1991 | Kasting et al. |
| 5,231,112 | A | 7/1993 | Janoff et al. |
| 5,482,711 | A | 1/1996 | Medenica |
| 2002/0132019 | A1 | 9/2002 | Kandil |
| 2005/0058735 | A1* | 3/2005 | Ahmad et al. ............... 424/764 |
| 2005/0214393 | A1 | 9/2005 | Kandil |

OTHER PUBLICATIONS

Berg, RW. Etiology and pathophysiology of diaper dermatitis. 1988. Advances in Dermatology. vol. 3, 75-97.*
Schlenk, H. and Holman, RT. Separation and stabilization of Fatty Acids by Urea complexes. Nov. 1950. Journal of American Chemical Society, vol. 72: 5001-5004.*
Nickavar, B., Mojab, F., Javidnia, K., and Amoli, M.A.R. Chemical Composition of the Fixed and Volatile Oils of *Nigella sativa* L. from Iran. Mar. 2003. Z. Naturforsch. vol. 58c, 629-631.*
Ali, B.H. and Blunden, G. Pharmacological and Toxicological Properties of *Nigella sativa*. 2003, Phytotherapy Research vol. 17, 299-305.*
Robinson, JK, Hernandez, C., Anderson, E.R. and Nickoloff, B. Topical and light-based treatments for basal cell carcinoma. Sep. 2003, Seminars in Cutaneous Medicine and Surgery. vol. 22, Issue 3: 171-176.*
Webster Ninth New Collegiate Dictionary. Definition of the term prevent, p. 1.*
Goreja, W.G. Black Seed: Nature's Miracle Remedy, 2003, pp. 33-42.*
Haresh et al. 1989. Effect of certain non-edible seed oils on growth regulation in dysdercus similis. J. Anim. Morphol. Physiol. 36(2): 209-218.
Ramadan and Mörsel, 2002, *Nahrung/Food*, 46 (4): 240-244.
Ramadan and Mörsel, 2002, *Eur. Food Res. Technol.*, 214: 202-206.
Ramadan and Mörsel, 2003, *J. Agric. Food Chem.*, 51: 6961-6969.
Zaoui et al., 2002, *Phytomedicine: Health & Medicial Complete*, 69-74.

* cited by examiner

*Primary Examiner*—Sreeni Padmanabhan
*Assistant Examiner*—Samira Jean-Louis
(74) *Attorney, Agent, or Firm*—Chalin Smith; Smith Patent Consulting (57) ABSTRACT

The present invention provides novel compositions comprising a *Nigella sativa* L. polyunsaturated fatty acid fraction. The present invention also provides novel compositions, particularly topical compositions, comprising octadecadienoic acid and/or octadecenoic acid. The present invention provides novel methods for treating and preventing fungal infections, bacterial infections, skin conditions, anal fissures, hemorrhoids, inflammation, pain, allergic reactions, and septic wounds by administering, preferably topically administering, an effective amount of a composition comprising octadecadienoic acid and/or octadecenoic acid, or a composition comprising the *Nigella sativa* L. polyunsaturated fatty acid fraction.

10 Claims, 2 Drawing Sheets

Percent Concentrations of Components Present in *Nigella sativa* L. Seeds After Treatments Described in Fig. 1

KEY:
( ) = Range of concentration.
[ ] = Prevalent Concentration.

POLYUNSATURATED FATTY ACID FRACTIONS OF *NIGELLA SATIVA* L. SEEDS

FIELD OF THE INVENTION

The present invention is generally directed to the field of medicine and pharmacology, particularly to compounds and compositions extracted from *Nigella sativa* L. seeds, and to methods of using the compounds and compositions. More particularly, the present invention is directed to a polyunsaturated fatty acid fraction of *Nigella sativa* L. and novel medicinal uses thereof.

BACKGROUND OF THE INVENTION

A variety of herbal and plant extracts are available today for treating many diseases affecting the human body. Some preparations have been known for thousands of years while others are just being discovered to have highly curative effects. Effective plant extracts are highly desired as a natural way to treat diseases. It is believed that natural preparations will not have an adverse effect on the body compared to synthetic preparations.

The *Nigella sativa* plant is cultivated for its seeds which are used for medicinal purposes. *Nigella sativa* L. seeds come from an herbaceous plant that belongs to the Ranunculaceae family. The plant is a dicotyledon and is cultivated in various parts of the world, especially in Eastern Mediterranean countries and also in India, Bangladesh, Turkey and Pakistan. It is also grown in other places having similar climates, such as East Africa, North Africa and the Middle East. The plant is characterized by an erect branched stem and alternating, finely divided, feathery, grayish-green leaves. The bluish-white, star-shaped flowers are terminal and solitary, and there are no petals. The fruit is a globase capsule with small black, rough seeds. Other species of *Nigella* include *Nigella arvensis* and *Nigella damascena*.

The seeds of *Nigella sativa* are known as Habbatul Baraka (meaning the seed of good fortune) and El Habba El Sawdaa (meaning Black Seed) in the Mediterranean region. The seeds are also known as Kalajira or Kalaoji and Black Cumin in the Indian subcontinent. *Nigella sativa* L. seeds have been used as a natural remedy for over 4,000 years in various parts of the world, particularly in the Near and Middle East. In the authentic tradition and sayings of the Prophet Muhammad (peace be upon him) which are documented in "Hadeeth" books he is quoted as saying: "In the Black Seed there is healing for every illness except death."

There is a need in the art for new pharmaceutical compounds and compositions that are derived from natural sources, like plants. The present invention is directed to this, as well as other, important ends.

SUMMARY OF THE INVENTION

The present invention provides novel compositions comprising a *Nigella sativa* L. polyunsaturated fatty acid fraction. The *Nigella sativa* L. polyunsaturated fatty acid fraction is primarily comprised of octadecadienoic acid and octadecenoic acid. The compositions are preferably formulated for topical administration and preferably contain a pharmaceutically acceptable carrier.

In one embodiment, the present invention provides a topical composition comprising a *Nigella sativa* L. polyunsaturated fatty acid fraction and a pharmaceutically acceptable carrier. The polyunsaturated fatty acid fraction is extracted from seeds of *Nigella sativa* L. in a manner that yields a fraction that is comprised primarily of octadecadienoic acid and octadecenoic acid and that is free from saturated fatty acids, sterols, volatile oils, and glyceryl esters. In a preferred embodiment, the octadecadienoic acid is present in the polyunsaturated fatty acid fraction in an amount ranging from about 60.7 to about 72.6% by weight, and the octadecenoic acid is present in the polyunsaturated fatty acid fraction in an amount ranging from about 23.8 to about 29.7% by weight.

The topical composition of the present invention may be formulated for topical administration as an ointment, cream, gel, powder, balm, lotion, liquid spray or aerosol, for example, or as the active ingredient of a transdermal patch.

In a further embodiment, the present invention provides novel uses for the *Nigella sativa* L. polyunsaturated fatty acid fraction including a methods for treating and preventing anal fissures and hemorrhoids, methods for treating or preventing skin conditions, methods for treating or preventing inflammation, pain of allergic reactions, methods for treating or preventing bacterial and fungal infections and/or modulating fungal and bacterial growth, by topically administering an effective amount of a composition comprising the *Nigella sativa* L. polyunsaturated fatty acid fraction.

These and other objects of the invention will be evident from the following description, taken together with the attached drawings and appended claims. It is to be understood that both the foregoing summary of the invention and the following detailed description are of a preferred embodiment, and not restrictive of the invention or other alternate embodiments of the invention.

DETAILED DESCRIPTION OF THE INVENTION

The present invention describes novel compositions, preferably topical compositions, comprising a *Nigella sativa* L. polyunsaturated fatty acid fraction. A "*Nigella sativa* L. polyunsaturated fatty acid fraction" refers to the polyunsaturated fatty acid fraction extracted from the seeds of *Nigella sativa* L. The *Nigella sativa* L. polyunsaturated fatty acid fraction is preferably extracted following the methods described in Example 1 and FIG. 1. Preferably, the "*Nigella sativa* L. polyunsaturated fatty acid fraction" comprises octadecadienoic acid and octadecenoic acid. The octadecadienoic acid is substantially in the form of cis-9,12-octadecadienoic acid (i.e., linoleic acid), while the octadecenoic acid is substantially in the form of cis-9-octadecenoic acid (i.e., oleic acid). Preferably, the *Nigella sativa* L. polyunsaturated fatty acid fraction comprises about 60.7 to about 72.6% by weight octadecadienoic acid and about 23.8 to about 29.7% by weight octadecenoic acid. One skilled in the art will recognize that the compounds described herein may exist in more than one isomeric and/or derivative form, such as, for example, a glyceryl esters.

In another embodiment, the *Nigella sativa* L. polyunsaturated fatty acid fraction further comprises cis-9,12,15-octadecatrienoic acid (i.e., linolenic acid) (preferably in an amount of about 0.83 to about 2.38% by weight); cis-11,14-eicosadienoic acid (preferably in an amount of about 1.2 to about 3.1% by weight); cis-9-tetradecenoic (i.e., myristoleic acid) (preferably in an amount of about 0.12 to about 0.25% by weight); cis-9-hexadecenoic (i.e., palmitoleic acid) (preferably in an amount of about 0.36 to about 1.2% by weight). One skilled in the art will recognize that the compounds described herein may exist in more than one isomeric and/or derivative form, such as, for example, a glyceryl ester.

In another embodiment, the present invention describes novel compositions comprising octadecadienoic acid, preferably cis-9,12-octadecadienoic acid. In another embodiment, the present invention describes novel compositions comprising octadecenoic acid, preferably cis-9-octadecenoic acid. In yet another embodiment, the present invention provides novel compositions comprising octadecadienoic acid and octadecenoic acid, preferably cis-9,12-octadecadienoic acid and cis-9-octadecenoic acid. One skilled in the art will recognize that the compounds described herein may exist in more than one isomeric and/or derivative form, such as, for example, a glyceryl ester.

Figure 1:
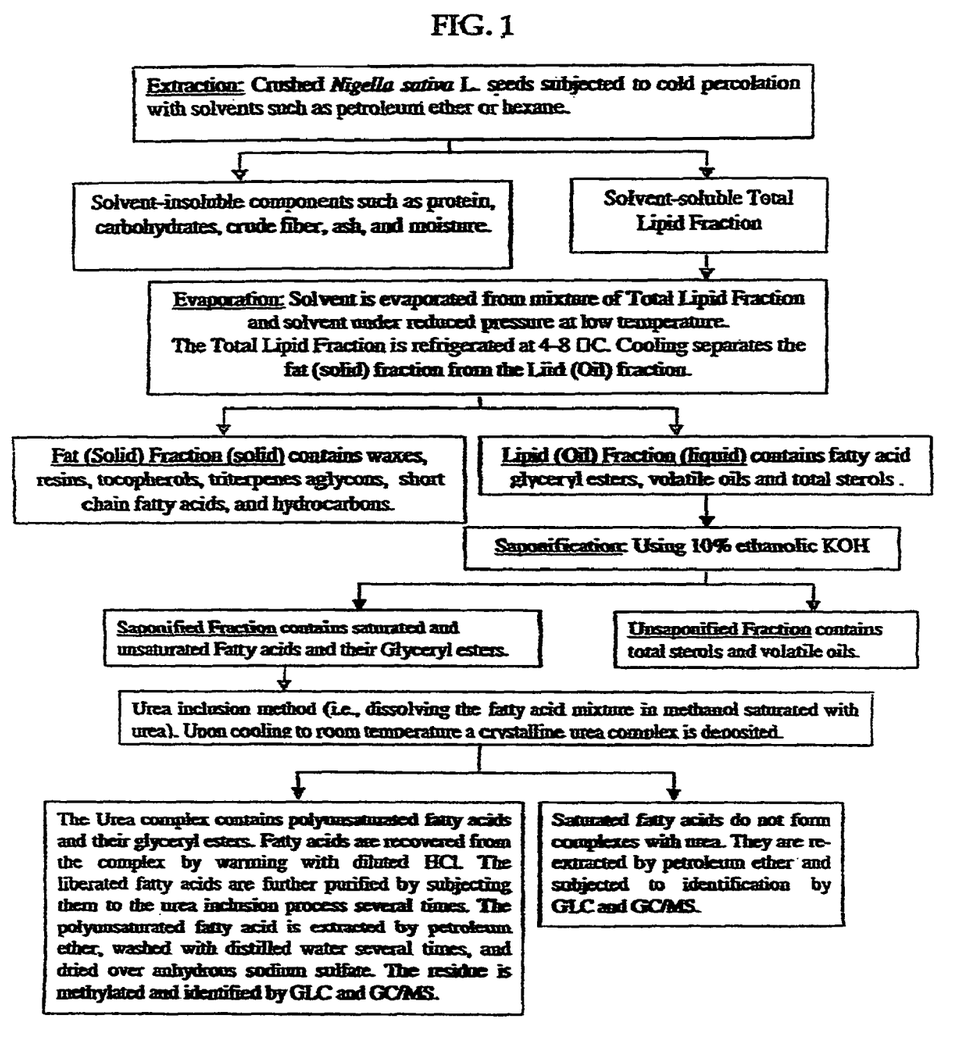
FIG. 1 shows the process for preparing the *Nigella sativa* L. polyunsaturated fatty acid fraction of the present invention from *Nigella sativa* L. seeds.
Figure 2:
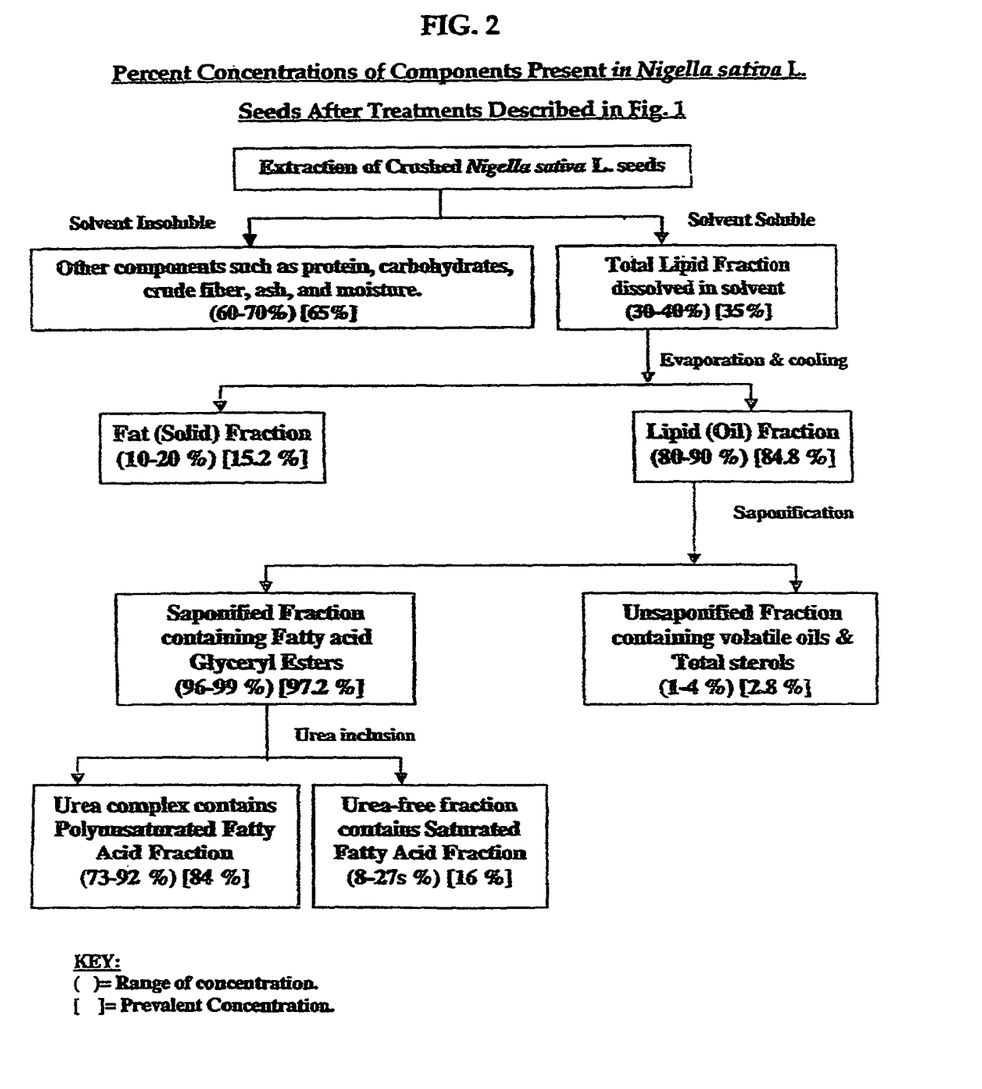
FIG. 2 shows the percent concentration of components present in *Nigella sativa* L. seeds after the various treatments and extractions described in FIG. 1.

In another embodiment, the *Nigella sativa* L. polyunsaturated fatty acid fraction is part of a total fatty acid fraction which is the saponified fraction described in Example 1 and FIGS. 1 and 2. The polyunsaturated fatty acid fraction is present in an amount of about 73% to about 92% by weight (preferably in an amount ranging from about 84% by weight) in the total fatty acid fraction. The saturated fatty acid fraction is present in an amount of about 8% to about 27% by weight (preferably in an amount ranging from about 16% by weight) of the total fatty acid fraction.

In the total fatty acid fraction, the *Nigella sativa* L. polyunsaturated fatty acid fraction comprises about 51 to about 61% by weight octadecadienoic acid (i.e., substantially in the form of cis-9,12-octadecadienoic acid (i.e., linoleic acid)); about 20 to about 25% by weight octadecenoic acid (i.e., substantially in the form of cis-9-octadecenoic acid (i.e., oleic acid)); about 0.7 to about 2% by weight cis-9,12,15-octadecatrienoic acid (i.e. linolenic acid); cis-11,14-eicosadienoic acid (preferably in an amount ranging from about 1 to about 2.6% by weight); cis-9-tetradecenoic (i.e., myristoleic acid) (preferably in an amount ranging from about 0.10 to about 0.21% by weight); and cis-9-hexadecenoic (i.e., palmitoleic acid) (preferably in an amount of about 0.30 to about 1.0% by weight). One skilled in the art will recognize that the compounds described herein may exist in more than one isomeric and/or derivative form, such as, for example, a glyceryl ester.

In the total fatty acid fraction, the saturated fatty acid fraction comprises about 11 to about 14% N-hexadecanoic acid (i.e., palmitic acid); about 0.1 to about 1% tetradecanoic acid (i.e., myristic acid); about 0.14 to about 3% eicosanoic acid (i.e., arachidic acid); about 0.5 to about 3.2% octadecanoic acid (i.e., stearic acid); and about 0.8 to about 1.3% tetracosanoic acid (i.e., lignoseric acid). One skilled in the art will recognize that the compounds described herein may exist in more than one isomeric and/or derivative form, such as, for example, a glyceryl ester.

In another embodiment, the *Nigella sativa* L. polyunsaturated fatty acid fraction is part of a lipid (oil) fraction which results from evaporating and cooling the solvent-extracted total lipid fraction as described in Example 1 and FIGS. 1 and 2. This lipid (oil) fraction is present in an amount of about 80 to about 90% (more preferably about 84.8%) of the total lipid fraction. The lipid (oil) fraction contains, in addition to the fatty acid fraction described above, volatile oils in an amount of about 0.1-1% (more preferably about 0.5%), and total sterols in an amount of about 1-3% (more preferably about 2.3%).

In a preferred embodiment, the present invention describes novel compositions comprising the *Nigella sativa* L. polyunsaturated fatty acid fraction of the present invention or compositions comprising octadecadienoic acid and/or octadecenoic acid in an amount ranging from about 1 to about 33% by weight based on 100% by weight of the composition. Preferably, the compositions comprise the *Nigella sativa* L. polyunsaturated fatty acid fraction of the present invention or the compositions comprise octadecadienoic acid and/or octadecenoic acid in an amount of about 10 to about 30% by weight; more preferably in an amount ranging from about 15 to about 28% by weight, more preferably in an amount ranging from about 18 to about 25% by weight, even more preferably about 20 to about 23% by weight.

The present invention provides novel methods for modulating fungal growth by administering, preferably topically administering, an effective amount of a composition comprising the *Nigella sativa* L. polyunsaturated fatty acid fraction of the present invention or an effective amount of a composition comprising octadecadienoic acid and/or octadecenoic acid. The growth of any fungi known in the art can be modulated with the compounds and compositions of the present invention. Exemplary fungi whose growth can be modulated include, but are not limited to, those from the genus *Candida* (e.g., *Candida albicans*), the genus *Microsporum* (e.g., *Microsporum canis, Microsporum gypseum*), the genus *Aspergillus* (e.g., *Aspergillus flavus, Aspergillus niger*), the genus *Penicillium* (e.g., *Penicillium* spp), the genus *Tinea* (e.g., *Tinea circinata, Tinea pedis, Tinea cruris, Tinea versicolor, Tinea axillaris, Tinea capitis*), the genus *Monilia*, the genus *Cladosporium*, the genus *Phialophora*, and the genus *Paracoccidioides* (e.g., *Paracoccidioides brasiliensis*).

"Modulating fungal growth" refers to killing or eliminating the fungi, reducing the amount of fungi (e.g., compared to the amount of fungi present before the compound or composition of the present invention was applied), or slowing the rate of growth of the fungi (e.g., compared to the rate of growth of the fungi absent the presence of the compound or composition of the present invention).

The present invention also provides novel methods for treating and preventing fungal infections in a patient in need thereof by administering, preferably topically administering, an effective amount of a composition comprising the *Nigella sativa* L. polyunsaturated fatty acid fraction of the present invention or an effective amount of a composition comprising octadecadienoic acid and/or octadecenoic acid. Any fungal infection known in the art can be treated or prevented with the compositions of the present invention. Preferably, the fungal infection is a fungal skin infection. Exemplary fungal infections that can be prevented or treated with the compositions of the present invention include, but are not limited to, those from the genus *Candida* (e.g., *Candida albicans*), the genus *Microsporum* (e.g., *Microsporum canis, Microsporum gypseum*), the genus *Aspergillus* (e.g., *Aspergillus flavus, Aspergillus niger*), the genus *Penicillium* (e.g., *Penicillium* spp), the genus *Tinea* (e.g., *Tinea circinata, Tinea pedis, Tinea cruris, Tinea versicolor, Tinea axillaris, Tinea capitis*), the genus *Monilia*, the genus *Cladosporium*, the genus *Phialophora*, and the genus *Paracoccidioides* (e.g., *Paracoccidioides brasiliensis*). One skilled in the art will appreciate that *Dermatophytoses* (e.g., ring worn/tinea) affect, for example, skin, hair and nails; *Aspergillus* affect, for example, ear, eyes, lungs and skin, and *Candida* affect, for example, the respiratory tract, the gastrointestinal tract, the urogenital tract, and skin. As used throughout the disclosure, "patient" refers to animals, preferably mammals, more preferably humans, and includes infants, children and adults, and males and females.

"Treating and preventing fungal infections" includes eliminating or curing the fungal infection, reducing the size or severity of the fungal infection (e.g., compared to the size or severity of the fungal infection before the compounds or compositions of the present invention were administered), and/or reducing the rate of growth of the fungal infection (e.g., compared to the rate of growth of the fungal infection in the absence of the compounds or compositions of the present invention).

The polyunsaturated long chain fatty acids in the *Nigella sativa* L. polyunsaturated fatty acid fraction described herein contain a hydrophobic chain with double bonds. Without intending to be bound by any theory of the invention, the double bond chain of the polyunsaturated fatty acids interacts with the ergosterol in the cell membrane of the fungus to produce a sterol-polyene complex. This interaction displaces the ergosterol from its normal phospholipid interaction in the cell membrane, which changes the physical composition of the cell membrane, thus causing fungicidal disruption of cellular integrity.

The present invention provides novel methods for modulating bacterial growth by administering, preferably topically administering, an effective amount of a composition comprising the *Nigella sativa* L. polyunsaturated fatty acid fraction of the present invention or an effective amount of a composition comprising octadecadienoic acid and/or octadecenoic acid. The growth of any bacteria known in the art can be modulated with the compounds and compositions of the present invention. Exemplary bacteria whose growth can be modulated include, but are not limited to, those from the genus *Staphylococcus* (e.g., *Staphylococcus aureus, staphyloccus pyogenes*), *Corynebacterium* (e.g., *Corynebacterium pyogenes*), *Streptococcus* (e.g., *Streptococcus pyogenes*), *Salmonella* (e.g., *Salmonella typhi murium*), *Escherichia* (e.g., *Escherichia coli*), *Pseudomonas* (e.g., *Pseudomonas aeroginosa*), and *Klebsiella* (e.g., *Klebsiella* spp.).

"Modulating bacterial growth" refers to killing or eliminating the bacteria, reducing the amount of bacteria (e.g., compared to the amount of bacteria present before the compound or composition of the present invention was applied), or slowing the rate of growth of the bacteria (e.g., compared to the rate of growth of the bacteria absent the presence of the compound or composition of the present invention).

The present invention also provides novel methods for treating and preventing bacterial infections in a patient in need thereof by administering, preferably topically administering, an effective amount of a composition comprising the *Nigella sativa* L. polyunsaturated fatty acid fraction of the present invention or an effective amount of a composition comprising octadecadienoic acid and/or octadecenoic acid. Any bacterial infection known in the art can be treated or prevented with the compounds or compositions of the present invention. Exemplary bacterial infections that can be prevented or treated with the compounds or compositions of the present invention include, but are not limited to, those from the genus *Staphylococcus* (e.g., *Staphyloccus aureus, staphyloccus pyogenes*), *Corynebacterium* (e.g., *Corynebacterium pyogenes*), *Streptococcus* (e.g., *Streptococcus pyogenes*), *Salmonella* (e.g., *Salmonella typhi murium*), *Escherichia* (e.g., *Escherichia coli*), *Pseudomonas* (e.g., *Pseudomonas aeroginosa*), and *Klebsiella* (e.g., *Klebsiella* spp.).

"Treating and preventing bacterial infections" includes eliminating or curing the bacterial infection, reducing the severity of the bacterial infection (e.g., compared to the severity of the bacterial infection before the compounds or compositions of the present invention were administered), and/or reducing the rate of growth of the bacterial infection (e.g., compared to the rate of growth of the fungal infection in the absence of the compounds or compositions of the present invention).

The present invention also provides novel methods for treating and preventing skin conditions in a patient in need thereof by administering, preferably topically administering, an effective amount of a composition comprising the *Nigella sativa* L. polyunsaturated fatty acid fraction of the present invention or an effective amount of a composition comprising octadecadienoic acid and/or octadecenoic acid. "Skin conditions" includes any skin conditions known in the art, including, but not limited to, for example, psoriasis, eczema, dermatitis, dry, scaly, itchy or flaky skin, diaper rash, athlete's foot, jock itch, scalp irritations, and dermal infections.

As used herein, the term "dermatitis" includes, but is not limited to, infantile seborrheic dermatitis, napkin dermatitis, contact dermatitis, atopic dermatitis, neurodermatitis, photodermatitis, urticaria, contact balanitis, hyperkeratosis, exfoliative dermatitis, and acne.

Without intending to be bound by any theory of the invention, the compositions of the present invention act as an antihistamine and regulate skin cell membrane functions, including modulating trans-epidermal water loss. With respect to dry skin, the compounds and compositions of the present invention produce eicosanoids. These important hormone-like compounds dampen inflammatory reactions in the skin. The polyunsaturated fatty acid fraction from *Nigella Sativa* seeds is considered a precursor to eicosanoids which produce leukotrienes and prostaglandins.

The present invention provides methods for treating or preventing inflammation, pain, and/or allergic reactions in a patient in need thereof by administering, preferably topically administering, an effective amount of a composition comprising the *Nigella sativa* L. polyunsaturated fatty acid fraction of the present invention or an effective amount of a composition comprising octadecadienoic acid and/or octadecenoic acid. 5-lipoxygenase and cyclooxygenase are responsible for the oxygenation of arachidonic acid and the formation of inflammatory products, e.g., leukotrienes, prostaglandins and thromboxanes. Without intending to be bound by any theory of the invention, the best way of explaining the antiinflammatory effects of the *Nigella sativa* L. polyunsaturated fatty acid fraction is that a competitive inhibition mechanism exists between the oxidant enzymes (e.g., 5-lipoxygenase and cyclooxygenase) and the polyunsaturated fatty acids. The polyunsaturated fatty acids may bind both enzymes instead of arachidonic acid, and thus inhibit the formation of prostaglandin, thromboxane and leukotriene synthesis. Polyunsaturated fatty acids also inhibit serotonine and histamine, both of which are inflammatory mediators. Using the compositions of the present invention provides additional amounts of polyunsaturated fatty acids, which increases the production of prostaglandins, which reduces inflammation by increasing the level of cAMP. This inhibits the release of arachidonic acid from stores and activates T-lymphocytes.

The present invention also provides methods for increasing permeability and integrity of cell membranes and normalizing the functions of the cell membranes (e.g. maintaining the physiological role of the cell membrane) by administering, preferably topically administering, an effective amount of a composition comprising the *Nigella sativa* L. polyunsaturated fatty acid fraction of the present invention or an effective amount of a composition comprising octadecadienoic acid and/or octadecenoic acid. The present invention is also directed to a preparation of a pharmaceutical formulation to ensure fluidity and stability of skin cell membrane as it is a structural component of cell membranes. Without intending to be bound by any theory of the invention, polyunsaturated fatty acids play an important role in the maintenance of epidermal integrity by intervening in the cohesion of the stratum corneum of the skin and in preventing transepidermal water loss. Polyunsaturated fatty acids are important constituents of and structural parts of cell membranes that affect the function of membrane-bound enzymes and transport systems, and modulating cellular immune responses.

The present invention also provides methods for regulating moisture loss from the skin and to protecting the skin from injury and infection by administering, preferably topically administering, an effective amount of a composition comprising the *Nigella sativa* L. polyunsaturated fatty acid fraction of the present invention or an effective amount of a composition comprising octadecadienoic acid and/or octadecenoic acid. "Regulating moisture loss from the skin" refers to preventing any moisture from leaving the skin and to reducing the amount of moisture that leaves the skin (e.g., compared to the amount of moisture that leaves the skin absent the compounds or composition of the present invention).

The present invention provides methods for treating and preventing anal fissures and/or hemorrhoids by administering, preferably topically administering, an effective amount of a composition comprising the *Nigella sativa* L. polyunsaturated fatty acid fraction of the present invention or an effective amount of a composition comprising octadecadienoic acid and/or octadecenoic acid. Anal fissures are an acute or chronic ulceration of the mucous membrane on the anal canal that causes a cycle of infection, spasm and pain.

The present invention provides methods for treating and preventing septic wounds or infected septic wounds by administering, preferably topically administering, an effective amount of a composition comprising the *Nigella sativa* L. polyunsaturated fatty acid fraction of the present invention or an effective amount of a composition comprising octadecadienoic acid and/or octadecenoic acid.

The present invention also provides methods for treating and preventing rheumatoid arthritis by administering, preferably topically administering, an effective amount of a composition comprising the *Nigella sativa* L. polyunsaturated fatty acid fraction of the present invention or an effective amount of a composition comprising octadecadienoic acid and/or octadecenoic acid.

The dosage regimen for treating the diseases described herein is selected in accordance with a variety of factors, including the age, weight, sex, and medical condition of the patient, the severity of the disease, the route of administration, pharmacological considerations such as the activity, efficacy, pharmacokinetic and toxicology profiles of the particular compound or composition used, whether a drug delivery system is used and whether the compound or composition is administered as part of a drug combination.

The compounds and compositions of the present invention can be administered topically, orally, parenterally, by inhalation (nasal or oral), vaginally, or rectally in dosage unit formulations containing conventional nontoxic pharmaceutically acceptable carriers, adjuvants, and vehicles, as desired. One skilled in the art will appreciate that the compounds described herein may be present in the form of various conventional pharmaceutically acceptable salts. The term parenteral as used herein includes subcutaneous, intravenous, intramuscular, intrasternal injection, or infusion techniques. Preferably, the compounds or compositions of the present invention are topically administered.

Injectable preparations, for example, sterile injectable aqueous or oleaginous suspensions may be formulated according to the known art using suitable dispersing or wetting agents, suspending agents (e.g., methylcellulose, Polysorbate 80, hydroxyethylcellulose, acacia, powdered tragacanth, sodium carboxymethylcellulose, polyoxyethylene sorbitan monolaurate and the like), pH modifiers, buffers, solubilizing agents (e.g., polyoxyethylene hydrogenated castor oil, Polysorbate 80, nicotinamide, polyoxyethylene sorbitan monolaurate, Macrogol, an ethyl ester of castor oil fatty acid, and the like) and preservatives. The sterile injectable preparation may also be a sterile injectable solution or suspension in a nontoxic parenterally acceptable diluent or solvent, for example, as a solution in 1,3-butanediol. Among the acceptable vehicles and solvents that may be used are water, Ringer's solution, and isotonic sodium chloride solution. In addition, sterile, total lipids are conventionally used as a solvent or suspending medium. For this purpose any bland total lipid may be used including synthetic mono- or diglycerides, in addition, fatty acids such as oleic acid find use in the preparation of injectables. The preparations can be lyophilized by methods known in the art.

Solid dosage forms for oral administration may include capsules, soft gel capsules, tablets, sublingual tablets, powders, granules and gels. In such solid dosage forms, the active compound(s) may be admixed with one or more inert diluents such as lactose or starch. As is normal practice, such dosage forms may also comprise other substances including lubricating agents such as magnesium stearate. In the case of capsules, tablets, and pills, the dosage forms may also comprise buffering agents. The tablets can be prepared with enteric or film coatings. For treating bronchial asthma in adults, the compositions of the present invention are preferably prepared in the form of a soft gel capsule.

Liquid dosage forms for oral administration can include pharmaceutically acceptable emulsions, solutions, suspensions, and syrups containing inert diluents commonly used in the art, such as water. Such compositions can also comprise adjuvants, such as wetting agents, emulsifying and suspending agents, and sweetening, flavoring, and perfuming agents. When pharmaceutical preparations of the present invention are prepared for treating infants or children, they are preferably prepared in a liquid dosage form. For example, in the methods of treating bronchial asthma described herein, the composition is preferably prepared in the form of a syrup when it is administered to infants or children.

For administration by inhalation (oral or nasal), the compositions of the invention can be delivered from an insufflator, a nebulizer or a pressured pack or other convenient mode of delivering an aerosol spray. Pressurized packs can include a suitable propellant. Alternatively, for administration by inhalation, the compositions can be administered in the form of a dry powder composition or in the form of a liquid spray.

Suppositories for vaginal, urethral, or rectal administration can be prepared by mixing the active compounds with suitable nonirritating excipients such as cocoa butter and polyethylene glycols that are solid at room temperature and liquid at body temperature.

For topical administration, the compounds or compositions of the invention can be formulated, for example, as an ointment, cream, gel, powder, balm (e.g., lip balm, stick deodorant), or lotion, or as the active ingredient of a transdermal patch. Topical administration can also be accomplished with a liquid spray, an aerosol, or via iontophoresis, or through the use of liposomes, microbubbles and/or microcapsules. Ointments and creams may be formulated, for example, with an aqueous or oily base with the addition of suitable thickening (e.g., PEG 4000, PEG 600, wax, hard paraffin) and/or gelling agents (e.g., hydroxypropyl cellulose). Lotions may be formulated with an aqueous or oily base and can also generally contain one or more emulsifying agents (e.g., wool wax alcohol, fatty acid glycol esters), stabilizing agents (e.g., polyoxyethylene sorbitan monolaurate, carboxy methyl cellulose), dispersing agents (e.g., sodium oleate, propylene glycol), suspending agents (e.g., methyl cellulose, chitosan, accacia, carboxymethyl cellulose, tragacanth, pectin), thickening agents, and/or coloring agents (e.g., dyes, lackes). Topical administration includes administration to the vulva and vagina.

Generally, a lotion is a suspension of finely divided active ingredient in a small amount of water. Lotions provide fast release of the active ingredient due to the soluble nature of the active ingredient and the water content. Lotions generally have short duration of action. Generally, an ointment is a semi-solid preparation that is more viscous and provides for slow release of the active ingredients due to longer duration of contact with the skin. Generally, a cream is a semi-solid preparation that contains a humectant and a higher percentage of water than an ointment. Creams are less viscous than ointments and provide for release of the active ingredients over a moderate period of time.

While the compounds and compositions of the invention can be administered as the sole active pharmaceutical agent in the methods described herein, they can also be used in combination with one or more compounds which are known to be therapeutically effective against the specific disease that one is targeting for treatment.

The present invention is described in terms of a *Nigella sativa* L. polyunsaturated fatty acid fraction. The methods for obtaining a *Nigella sativa* L. polyunsaturated fatty acid fraction can also be followed to obtain a *Nigella arvensis* polyunsaturated fatty acid fraction, a *Nigella damascena* polyunsaturated fatty acid fraction, or a polyunsaturated fatty acid fraction from any other species of *Nigella*. Moreover, a *Nigella arvensis* polyunsaturated fatty acid fraction and/or a *Nigella damascena* polyunsaturated fatty acid fraction can be used for modulating fungal growth, for treating and preventing fungal infections, for modulating bacterial growth, for treating and preventing bacterial infections, for treating and preventing skin conditions, for treating and preventing inflammation, pain and/or allergic reactions, for increasing permeability and integrity of cell membranes and normalizing the functions of the cell membranes, for regulating moisture loss from the skin, for protecting the skin from injury and infection, for treating and preventing anal fissures and/or hemorrhoids, for treating and preventing septic wounds or infected septic wounds, and/or for treating and preventing rheumatoid arthritis as described in detail herein.

EXAMPLES

The following examples are for purposes of illustration only, and are not intended to limit the scope of the appended claims.

Example 1

The process for preparing the *Nigella sativa* L. polyunsaturated fatty acid fraction of the present invention from *Nigella sativa* L. seeds is outlined in FIG. 1, and discussed below.

4 kilograms of crushed *Nigella sativa* L. seeds were successively extracted in a percolator until exhaustion with various solvents in order of increasing polarity. The solvents used, in order, were petroleum ether (40-60° C.) or hexane, ether, chloroform, ethylacetate, acetone, ethanol, methanol and water.

A slurry composed of 1 part silica gel G. and 2 parts water was spread on clean glass plates at a thickness of 0.25-0.3 mm. The plates were air-dried for 30 minutes, activated in an air-drying oven at 110° C. for 30 minutes, and then kept in a dissector until use.

5.0 grams of the intermediate product (e.g., the petroleum ether extract) prepared by extraction were dissolved in petroleum ether and mixed with about 5 grams of silica gel 60 (For Column) to form a homogenous mixture, were finely powdered, and applied on the top of a column (3×60 cm) packed with silica gel 60 (250 grams). Elution was performed using the best solvent system as indicated by TLC, in this case ether:benzene (85:15). Fractions of 50 ml were collected and the similar fractions, as indicated by TLC, using different solvent systems, preferably ether:benzene (85:15), and vanillin $H_2SO_4$ spray reagent, were pooled together and then evaporated under reduced pressure.

20 grams of the intermediate product were saponified by refluxing with 200 ml of 10% ethanolic KOH and 80 ml of benzene for 8 hours. The solvent was then evaporated under reduced pressure. The residue containing the potassium salt of the fatty acid was treated with dilute HCl to liberate the free fatty acids. The fatty acids were extracted with petroleum ether or hexane, washed with water and dried over anhydrous sodium sulfate. The solvent (petroleum ether or hexane) was removed under reduced pressure. The residue containing the polyunsaturated fatty acids was dissolved in warm methanol saturated with urea (about 16 grams/100 ml). A small portion of isopropanol was added to help the solubilization of the polyunsaturated fatty acids. Upon cooling to room temperature, crystalline urea complex was deposited which was then filtered off and dried. The product was recrystallized from methanol or isopropanol. The polyunsaturated fatty acids were liberated from the complex by warming with dilute HCl. The free fatty acids were extracted with petroleum ether or hexane, washed with water and dried over anhydrous sodium sulfate. The solvent was removed under reduced pressure to yield the free fatty acids. The liberated fatty acids were further purified by subjecting them to the urea inclusion process several times.

To facilitate introduction to GC pure polyunsaturated fatty acids were converted to the corresponding volatile esters. The polyunsaturated fatty acids were methylated by addition of 20 ml methyl alcohol/$H_2SO_4$ (3% $H_2SO_4$ in methanol), and refluxed for 5 hours. The methyl ester of polyunsaturated fatty acids were extracted with ether, washed with water and dried over anhydrous sodium sulfate.

The polyunsaturated fatty acid esters prepared from the polyunsaturated fatty acid fraction of *Nigella sativa* L. were subjected to GC/MS analysis under the following conditions: carrier gas: nitrogen; column: glass 200 cm×3 mm (internal diameter); temperature: 200° C. isothermal.

To determine the degree of unsaturation of the oil, 5 ml of the total lipid of *Nigella sativa* L. seeds were dissolved in a few ml of $CH_2Cl_2$ (dichloromethane) and kept in contact with known excess of Hanus reagent for 1-2 hours in a dry stoppered container moistened with KI solution. A known excess of KI solution was added, diluted with water and liberated $I_2$ was titrated with standard sodium thiosulfate solution using starch as an indicator.

The fatty acid methyl esters were prepared by methylation of the lipids according to IUPAC Method 2.301 (IUPAC, Standard Methods for the Analysis of Oil, Fats, and Derivatives, $6^{th}$ ed., Pergamon Press, Oxford, 1979); Carpenter, A. P. Jr., Determination of Tocopherols in Vegetable Oils. *J. Am. Oil Chem. Soc.*, 56:668-671 (1979); Otles, S., Comparative Determinations of vitamins B1 and B2 in food by using enzymes, *Z. Lebensm.-Unters. Forsch.*, 193:347-350 (1991). Gas chromatography of the methyl esters was conducted on a Packard GC apparatus (Model 439), equipped with a hydrogen flame ionization detector. The carrier gas was nitrogen, at a flow rate of 30 ml/minute, a glass column of 200 cm×0.5 cm (outside diameter) packed with DEGS (diethylene glycol succinate) 10% on 80-100 mesh chromosorb.

The composition of the polyunsaturated fatty acid fraction is shown in Table 1.

TABLE 1

| No. | IUPAC Name | Common | % by weight in fraction | Abbreviated Structure |
|---|---|---|---|---|
| 1. | cis-9,12-octadecadienoic acid | Linoleic acid | 60.7-72.6% | C18:2 |
| 2. | cis-9-octadecenoic acid | Oleic acid | 23.8-29.7% | C18:1 |
| 3. | cis-11,14-eicosadienoic acid |  | 1.2-3.1% | C20:2 |
| 4. | cis-9,12,15-octadecatrienoic acid | Linolenic acid | 0.83-2.38% | C18:3 |
| 5. | cis-9-hexadecenoic acid | Palmitoleic acid | 0.36-1.2% | C16:1 |
| 6. | cis-9-tetradecenoic acid | Myristoleic acid | 0.12-0.25% | C14:1 |

Example 2

The following pharmaceutical formulation was prepared in the form of an ointment in a washable base (for oil). Each 20 grams of ointment contained the following: Active ingredient (4 g); Polyethylene glycol 400 (PEG) (2.8 g); Polyethylene glycol 4000 (PEG) (7.42 g); Purified Water (5.108 ml); Tween 80 (0.4 g); Butylated hydroxy anisol (BHA) (0.012 g); Butylated hydroxy toluene (BHT) (0.012 g); Methyl paraben (0.24 g); Propyl paraben (0.008 g); The "active ingredient" refers to the Nigella sativa L. polyunsaturated fatty acid fraction described herein.

Example 3

The following pharmaceutical formulation was prepared in the form of a cream. Each 20 grams of cream contained the following: Active ingredient (4 g); Cetyl Alcohol (1.84 g); Glyceryl monostearate (5.07 g); Span 80 (0.05 g); Purified Water (6.257 ml); Tween 80 (0.229 g); Methyl cellulose (0.206 g); Propylene glycol (2.3 g); Butylated hydroxy anisol (BHA) (0.013 g); Butylated hydroxy toluene (BHT) (0.013 g); Methyl paraben (0.013 g); Propyl paraben (0.009 g). The "active ingredient" refers to the Nigella sativa L. polyunsaturated fatty acid fraction described herein.

Example 4

The following pharmaceutical formulation was prepared in the form of an ointment. Each 15 grams of the ointment contained the following: Active Ingredient (3 g); stearyl alcohol (0.8 g); beeswax (1.5 g); anhydrous lanolin (4 g); vaseline (5.5 g); BHT (0.1 g); BHA (0.1 g). The "active ingredient" refers to the Nigella sativa L. polyunsaturated fatty acid fraction described herein. The stearyl alcohol is as an emollient and stabilizer. The beeswax is an emulsifying agent and stabilizer. The anhydrous lanolin is an emulsifying agent, an emollient, and absorbs water to facilitate the spreading of the ointment on a wet area. The vaseline and anhydrous lanolin formed the oleaginous ointment base which is occlusive and enhances spreading. BHT (butylated hydroxytoluene) and BHA (butylated hydroxyanisol) are used as antioxidants and preservatives.

Example 5

Determination of $LD_{50}$ $LD_{50}$ of the Nigella sativa L. polyunsaturated fatty acid fraction was performed as described by Sun, Science, 222: 1106 (1983). Willis, J. Pharm. Pharmacol., 21:126 (1969). In this experiment, 8 groups of 5 mice (weight 20 g) were used for each polyunsaturated fatty acid fraction. One group was left as a control, while the other 7 groups were injected subcutaneously with the polyunsaturated fatty acid fraction. The toxic symptoms, mortality rate, and post-mortem findings in each group were recorded. $LD_{50}$ were calculated according to the following formula: $LD_{50}=D_m-[(\Sigma(Z \times d)) \div N]$, where $D_m$ was the largest dose which killed all animals, Z was the mean of dead animals in 2 successive groups, d was the constant factor between 2 successive groups, N was the number of animals in each group, and $\Sigma$ was the sum of (Z×d).

The toxic effect, dead animals, MLD and $LD_{50}$ of the studied drug were recorded in Table 2. The drug doses less than 1750 mg/100 grams body weight failed to kill mice within 24 hours of their subcutaneous injection. The minimum lethal dose (MLD) and $LD_{50}$ were 1750 and 2500 mg/100 grams body weight, respectively.

Mice treated with the Nigella sativa L. polyunsaturated fatty acid fraction showed muscle tremors, shallow rapid respiration and abdominal cramps as the main symptoms of toxicity. Post-mortem examination of the dead mice showed congestion of the liver, heart and kidneys.

TABLE 2

Doses, number of dead animals and constant factors of the Nigella sativa L. polyunsaturated fatty acid fraction

| Dose (mg/ 100 g.b.w.) | No. of mice | dead mice | d | z | (z × d) |
|---|---|---|---|---|---|
| 1250 | 5 | 0 |  |  |  |
| 1750 | 5 | 1 | 500 | 0.5 | 250 |
| 2250 | 5 | 2 | 500 | 1.5 | 750 |
| 2750 | 5 | 3 | 500 | 2.5 | 1250 |
| 3500 | 5 | 4 | 500 | 3.5 | 1750 |
| 3750 | 5 | 5 | 500 | 4.5 | 2250 |

Example 6

The anti-histamine effects of the Nigella sativa L. polyunsaturated fatty acid fraction on induced bronchospasm in guinea pigs was evaluated using the methods described by Armitage et al. Brit. J. Pharmacol., 16:59-76 (1961). Willis, J. Pharm. Pharmacol., 21:126 (1969).

The prophylactic anti-allergic effects were evaluated in guinea pigs (300-400 grams). The animals were divided into 5 groups (10 animals each) and treated i.p. as follows: (1) animals treated with saline (control); (2) animals treated with diphenydramine (239 mg/kg/day) (3) animals treated with 50 mg/kg polyunsaturated fatty acid fraction; (4) animals treated with 100 mg/kg polyunsaturated fatty acid fraction; and (5) animals treated with 150 mg/kg polyunsaturated fatty acid fraction.

Animals were exposed 30 minutes after their i.p. injection of diphenydramine and polyunsaturated fatty acid fraction to histamine aerosol (1%) for 3 minutes. Bronchospasm and loss of rightening after 30, 60 and 90 minutes was calculated according to the following formula (Dawson and Sweatman, Br. J. Pharmacol., 71:387-398 (1980)):

$$\% \text{ Protection} = 1 - \frac{600 - \text{Preconvulsive Time}}{600} \times 100$$

Table 3 shows the prophylactic effects of the *Nigella sativa* L. polyunsaturated fatty acid fraction on histamine-induced bronchospasm in guinea pigs. The *Nigella sativa* L. polyunsaturated fatty acid fraction produced no allergic effects. The *Nigella sativa* L. polyunsaturated fatty acid fraction in amounts of 100 mg/kg and 150 mg/kg protected guinea pits from histamine-induced bronchospasm.

TABLE 3

The effect of the *Nigella sativa* L. polyunsaturated fatty acid fraction on protection from histamine-induced bronchospasm in guinea pigs (n = 10)

| Group | Dose (mg/kg) | % protection 30 minutes | % protection 60 minutes | % protection 90 minutes |
|---|---|---|---|---|
| Control | — | 0 | 0 | 0 |
| diphenhydramine | 239 | 100 | 100 | 90 |
| *Nigella sativa* L. polyunsaturated fatty acid fraction | 50 | 0 | 0 | 0 |
| *Nigella sativa* L. polyunsaturated fatty acid fraction | 100 | 50 | 70 | 60 |
| *Nigella sativa* L. polyunsaturated fatty acid fraction | 150 | 90 | 80 | 80 |

Example 7

Antifungal and Antibacterial Tests

The measure of the MIC (minimum inhibitory concentration) values was determined from the recommendations of National Committee for Clinical Laboratory Standards, "Reference Method for Growth Dilution Antifungal Susceptibly Testing for Yeast. Proposed Standards Documents" M27-P, Villanova, Pa. (1992). *Nigella sativa* L. polyunsaturated fatty acid fractions were dissolved in DMSO to make a concentration of 250 mg/ml. The *Nigella sativa* L. polyunsaturated fatty acid fractions were then diluted in a two-fold manner in the medium (SD broth) in 96 microwell plates, and 100 microliters were placed in each well. The fungal organisms, taken from SDA plates, were suspended in normal saline to obtain T %=75-77% at 530 nm, which is equal to $10^6$ CFU/ml. The fungal suspension was diluted 1,000 times in the medium and 100 microliter aliquots were added to each well. The 96 well plates were incubated in 35° C. for 24-96 hours. The MIC was defined as the minimum concentration of the agent that showed full inhibition of the fungus by a visual observation. All tests were repeated twice.

The following fungal species were used: molds (*Aspergillus flavus*, *Asperfillus niger*, and *Penicillium* spp.); dermatophytes (*Microsporum gipseum* and *Microsporum canis*); and yeast (*Candida albicans*).

Data in Table 4 show that the *Nigella sativa* L. polyunsaturated fatty acid fraction exerted a marked inhibitory effect on the growth of the following fungi in descending order: *Candida albicans*, *Microsporum canis*, *Aspergillus niger*, *Microsporum gypseum*, *Aspergillus flavus*, and *Penicillium* spp.

TABLE 4

Antifungal activity of the *Nigella sativa* L. polyunsaturated fatty acid fraction

| Microorganism | Concentration (mg/ml) | Zone of Inhibition (mm) |
|---|---|---|
| *Candida albicans* | 1 | 13.0 ± 0.16 |
|  | 5 | 17.2 ± 0.33 |
|  | 10 | 21.7 ± 0.57 |
|  | 25 | 30.1 ± 0.88 |
|  | 50 | 39.5 ± 1.87 |
| *Aspergillus niger* | 1 | 12.5 ± 0.10 |
|  | 5 | 14.6 ± 0.16 |
|  | 10 | 19.8 ± 0.33 |
|  | 25 | 25.2 ± 0.88 |
|  | 50 | 33.7 ± 0.67 |
| *Aspergillus flavus* | 1 | 11.5 ± 0.33 |
|  | 5 | 13.5 ± 0.44 |
|  | 10 | 16.5 ± 0.51 |
|  | 25 | 19.7 ± 0.56 |
|  | 50 | 25.0 ± 0.67 |
| *Penicillium* spp. | 1 | — |
|  | 5 | 12.5 ± 0.16 |
|  | 10 | 15.3 ± 0.28 |
|  | 25 | 19.5 ± 0.33 |
|  | 50 | 22.7 ± 0.88 |
| *Microsporum canis* | 1 | 14.0 ± 0.16 |
|  | 5 | 18.5 ± 0.33 |
|  | 10 | 20.0 ± 0.28 |
|  | 25 | 27.2 ± 0.57 |
|  | 50 | 35.3 ± 0.58 |
| *Microsporum gypseum* | 1 | 11.0 ± 0.00 |
|  | 5 | 13.2 ± 0.33 |
|  | 10 | 16.3 ± 0.16 |
|  | 25 | 21.0 ± 0.88 |
|  | 50 | 32.0 ± 0.67 |

In vitro KB cell cytotoxicity (TD 50 g/ml) was determined for a few of the extracts that showed better antifungal activity. The MTT method was performed according to Hansen et al, *J. Immunol. Methods*, 119:203-210 (1975). The values are the average of three separate experiments. The anti-bacterial activity of the tested isolates was detected in vitro using the bore method. The nutrient agar medium containing one bacterial strain was poured into sterilized petri-dishes, each 20×120 mm, then left for 10 minutes to dry. Using the borer No. 5, a central bore was made in each plate, then another 4 bores were arranged around it. The effect of different concentrations of the tested isolates on certain microorganisms was tested in 2 plates. The plates were incubated at 37° C. for 24 hours and the MIC was determined.

The bacteria tested were as follows: gram positive bacteria (*Staphylococcus aureus*, *Corynebacterium pyogenes*, *Streptococcus pyogenes*); and gram negative bacteria (*Salmonella typhi*, *Escherichia coli*, *Pseudomonas aeroginosa*). The results of the experiments are shown in Table 5 below.

TABLE 5

Antibacterial activity of the polyunsaturated fatty acid fraction of *Nigella Sativa* L.

| Microorganism | Concentration (microgram/ml) | Diameter of Zone of Inhibition (mm) |
|---|---|---|
| *Staph. aureus* | 10 | — |
|  | 50 | — |
|  | 100 | 11.5 ± 0.28 |
|  | 1000 | 14.5 ± 0.33 |
|  | 5000 | 17.0 ± 0.00 |
|  | 10000 | 18.5 ± 0.57 |

TABLE 5-continued

Antibacterial activity of the polyunsaturated fatty acid fraction of *Nigella Sativa* L.

| Microorganism | Concentration (microgram/ml) | Diameter of Zone of Inhibition (mm) |
|---|---|---|
| *Strept. pyogenes* | 10 | — |
| | 50 | 10.5 ± 0.28 |
| | 100 | 12.5 ± 0.00 |
| | 1000 | 14.0 ± 0.16 |
| | 5000 | 19.0 ± 0.28 |
| | 10000 | 23.5 ± 0.47 |
| *C. pyogenes* | 10 | — |
| | 50 | — |
| | 100 | 12.0 ± 0.28 |
| | 1000 | 14.5 ± 0.16 |
| | 5000 | 17.0 ± 0.68 |
| | 10000 | 18.5 ± 0.57 |
| *E. Coli* | 10 | — |
| | 50 | — |
| | 100 | 12.0 ± 0.00 |
| | 1000 | 15.5 ± 0.57 |
| | 5000 | 18.7 ± 0.68 |
| | 10000 | 21.0 ± 0.88 |
| *S. Typhi murium* | 10 | — |
| | 50 | — |
| | 100 | 11.0 ± 0.00 |
| | 1000 | 13.2 ± 0.16 |
| | 5000 | 15.5 ± 0.46 |
| | 10000 | 17.0 ± 0.16 |
| *Klebsiella* spp. | 10 | — |
| | 50 | — |
| | 100 | 12.2 ± 0.16 |
| | 1000 | 14.5 ± 0.47 |
| | 5000 | 17.2 ± 0.33 |
| | 10000 | 18.5 ± 0.57 |
| *P. aeruginosa* | 10 | — |
| | 50 | 11.5 ± 0.28 |
| | 100 | 13.0 ± 0.16 |
| | 1000 | 16.5 ± 0.97 |
| | 5000 | 20.0 ± 0.57 |
| | 10000 | 22.7 ± 0.88 |

The comparative antibacterial activity of ampicillin and the *Nigella sativa* L. polyunsaturated fatty acid fraction against certain bacterial strains (*Streptococcus pyogenes, Corynebacterium pyogenes* and *Salmonella typhi murium*) was preformed in vitro using the bore method as described by Cooper and Woodman (1964) as previously described. The effect of ampicillin (1 μg/mL) and the *Nigella sativa* L. polyunsaturated fatty acid fraction (at 1 mg/ml) on the previously mentioned bacteria was tested.

The antibacterial effects of ampicillin (1 μg/mL) and the *Nigella sativa* L. polyunsaturated fatty acid fraction (1 mg/ml) on the bacteria is shown in Table 6. The *Nigella sativa* L. polyunsaturated fatty acid fraction at 1 mg/mL was almost equipotent to ampicillin (1 μg/mL) against *Streptococcus pyogenes, Corynebacterium pyogenes* and *Salmonella typhi murium*.

TABLE 6

In vitro studies of ampicillin (1 μg/mL) and the *Nigella sativa* L. polyunsaturated fatty acid fraction (1 mg/mL) against bacterial strains.

| Strain | Diameter of Zone of Inhibition (mm) | |
|---|---|---|
| | Ampicillin (1 μg/mL) | *Nigella sativa* L. polyunsaturated fatty acid fraction (1 mg/mL) |
| *Streptococcus pyogenes* | 26.7 ± 0.3 | 25.7 ± 0.3 |
| *Corynebacterium pyogenes* | 44.7 ± 0.8 | 45.5 ± 0.7 |
| *Salmonella typhi murium* | 13.1 ± 0.2 | 14.30 ± 0.0 |

Data are the mean ± S.E. of 4 observations.

Example 8

Phase I Clinical Study

The objective of the study was to assess the safety of the *Nigella sativa* L. polyunsaturated fatty acid fraction in humans. Ten healthy male volunteers were selected for the study. All subjects were screened according to their medical history (including concomitant medication history), a physical examination and laboratory investigation (e.g., chest x-ray, ECG, liver and kidney function tests, and urine for glucosuria), and a thorough skin examination. The healthy male subjects were 25 to 35 years old, were free from skin diseases, and had fair to dark complexions. Any volunteers with skin lesions, diabetes, neurological disorders, or with emotional or psychological instability were excluded from the study. Prior to the trial the volunteers signed consent forms.

The volunteers were asked to topically apply the cream described in Example 3 (containing the *Nigella sativa* L. polyunsaturated fatty acid fraction) in an amount of about 0.5 grams to an area about 5 cm in diameter on the medial aspect of the skin of the left arm twice daily for four weeks. They were hospitalized for 48 hours where all their vital signs were monitored and laboratory investigations (including liver and kidney function tests, hematological studies, urine and stool analysis, ECG and chest x-ray) were done immediately before and by the end of the period of administration. Volunteers were allowed to attend the outpatient clinic of the hospital once weekly for check-ups. On the 28th day, they were readmitted for clinical and laboratory evaluations.

The results of the study revealed no local irritation or sensitization. Physical examination and laboratory investigations carried out at the end of the fourth week revealed no statistically different changes. Based on the investigation, the topical cream in Example 3 was well tolerated in all the volunteers enrolled in the study without any observable local or systemic side effects.

Example 9

Phase II Clinical Study

The objective of the trial was to study the effectiveness of the cream described in Example 3 in the treatment of superficial fungal skin infections.

264 patients with fungal skin infections completed the trial. They were selected from the outpatient clinics of some hospitals in Cairo, Egypt. Patients were chosen according to the clinical and laboratory diagnosis. Patients were 3 months to 71 years old, and consisted of 179 men (68%) and 85 women (32%). All the subjects were screened according to their medical history and a physical examination and laboratory investigation (e.g., scraping of the fungal lesions and urine for glucosuria). Patients were excluded from the study if they were diabetics (as indicated by renal glucosuria), had emotional or psychological instability, had hepatic or renal diseases, and/or were under immunosuppressive agents, such as corticosteroids.

Patients willing to participate in the study had to complete a physical examination and laboratory investigations. Patients enrolled in the study were given the cream described in Example 3 according to their lesions twice daily (morning and evening) for 2-4 weeks. Patients were followed up once weekly. Patients' urine was tested for glucosuria and patients' lesions were scraped.

The patients had at least one of the following fungal skin infections: *Tinea circinata, Tinea pedis, Tinea cruris, Tinea versicolor, Tinea axillaris, Tinea capitis*, and/or *Monilia*.

Of the 264 patients who completed the trial, 179 showed a complete cure (68%), 34 patients were improved (13%) and 51 patients (19%) did not improve. The data is presented in Table 7. Complete cure was evidenced by a clinical and mycological cure as evidenced by scraping and culture. Improved was defined as a clinical cure, where fungi were still detected by scraping. No response was evidenced by neither clinical nor mycological improvement occurred.

TABLE 7

Effect of the *Nigella sativa* L. polyunsaturated fatty acid fraction on superficial fungal skin infections.

| | | complete cure | | improvement | | no response | |
|---|---|---|---|---|---|---|---|
| Infection | # of patients | # of patients | % response | # of patients | % response | # of patients | % response |
| *T. circinata* | 60 | 43 | 72 | 10 | 17 | 7 | 12 |
| *T. pedis* | 29 | 21 | 72 | 2 | 7 | 6 | 21 |
| *T. cruris* | 44 | 34 | 77 | 6 | 14 | 4 | 9 |
| *T. versicolor* | 26 | 9 | 35 | 3 | 12 | 14 | 54 |
| *T. axillaris* | 9 | 7 | 78 | 1 | 11 | 1 | 11 |
| *T. capitis* | 79 | 51 | 65 | 9 | 11 | 19 | 24 |
| *Monilia* | 17 | 14 | 82 | 3 | 18 | 0 | 0 |
| Total | 264 | 179 | 68 | 34 | 13 | 51 | 19 |

Example 10

Phase III Clinical Study

To compare the efficacy of the cream in Example 3 with that of a well known antifungal, DAKTACORT®, additional patients were recruited using the same criteria described in Example 9 above. DAKTACORT® contains 2% miconazole nitrate and 1% hydrocortisone, and is commercially available from Janssen-Cilag. The patients were given DAKTACORT® cream according to their lesions twice daily for 2-4 weeks.

In the group using the cream in Example 3, 30 patients (63%) exhibited complete cure, 8 patients (18%) showed improvement, and 10 patients (21%) did not respond.

In the DAKTACORT® group, 19 patients (54%) exhibited complete cure, 9 patients (26%) showed improvement, and 7 patients (20%) did not respond.

The results of the double-blind study are shown in the table below.

TABLE 8

| | | no response | | improvement | | complete cure | |
|---|---|---|---|---|---|---|---|
| Infection | Cream | # of patients | % response | # of patients | % response | # of patients | % response |
| *T. axillaris* | Daktacort ® | 0 | 0 | 3 | 60 | 2 | 40 |
| | Example 3 | 1 | 12.5 | 1 | 12.5 | 6 | 75 |
| Moniliasis | Daktacort ® | 0 | 0 | 0 | 0 | 5 | 100 |
| | Example 3 | 1 | 12.5 | 1 | 12.5 | 6 | 75 |
| *T. pedis* | Daktacort ® | 2 | 40 | 1 | 20 | 2 | 40 |
| | Example 3 | 2 | 25 | 1 | 12.5 | 5 | 62.5 |

TABLE 8-continued

| Infection | Cream | no response | | improvement | | complete cure | |
|---|---|---|---|---|---|---|---|
| | | # of patients | % response | # of patients | % response | # of patients | % response |
| T. versicolor | Daktacort ® | 3 | 60 | 1 | 20 | 1 | 20 |
| | Example 3 | 3 | 37.5 | 2 | 25 | 3 | 37.5 |
| T. circinata | Daktacort ® | 0 | 0 | 1 | 20 | 4 | 80 |
| | Example 3 | 1 | 20 | 0 | 0 | 4 | 80 |
| T. cruris | Daktacort ® | 0 | 0 | 2 | 40 | 3 | 60 |
| | Example 3 | 0 | 0 | 2 | 40 | 3 | 60 |
| T. capitis | Daktacort ® | 2 | 40 | 1 | 20 | 2 | 40 |
| | Example 3 | 2 | 33 | 1 | 17 | 3 | 50 |
| Total | Daktacort ® | 7 | 20 | 9 | 26 | 19 | 54 |
| | Example 3 | 10 | 21 | 8 | 18 | 30 | 63 |

Example 11

To be useful in treating anal fissures, a drug should promote wound healing, have an analgesic property, have anti-inflammatory action, have antiseptic and/or antibacterial activity, and/or have no sensitizing or allergic reactions. The objectives of the studies described in examples 11-14 on the composition in Example 4 were to determine the effect of *Nigella sativa* L. polyunsaturated fatty acid fraction on septic wound healing, the analgesic effects of the *Nigella sativa* L. polyunsaturated fatty acid fraction, the anti-inflammatory effect of the *Nigella sativa* L. polyunsaturated fatty acid fraction, the antibacterial effect of the *Nigella sativa* L. polyunsaturated fatty acid fraction, the anti-allergic effect of the *Nigella sativa* L. polyunsaturated fatty acid fraction, and to evaluate the chronic toxicity and teratogenecity of the *Nigella sativa* L. polyunsaturated fatty acid fraction. The results were statistically analyzed as explained by Snedecor (1969).

Twenty male and female guinea pigs (400-600 grams) were divided into 4 groups (5 animals/group) as follows. The first group (control group) was treated by saline dressings. The second group was treated by acriflavine (1%)-terramycin dressings. Acriflavine is a natural dye used as an antiseptic. The flavines (acriflavine and proflavine) stain the skin yellow, and are used at a strength of 1 in 1000 for pre-operative skin sterilization, etc., and as creams for wounds and burns (Jones, *Pharmacology For Student and Pupil Nurses and Students in Associated Professions,* 2nd Ed., The English Language Book Society and William Heinemann Medical Books, Ltd., London, page 171 (1987)). The third group was treated with the *Nigella sativa* L. polyunsaturated fatty acid fraction (1%) dressings. The fourth group was treated with a composition comprising the *Nigella sativa* L. polyunsaturated fatty acid fraction (5%) dressings.

A 2 cm length surgical incision was induced in each animal, and was infected with inocula of *Staphylococcus pyogenes* ($10^6$) The animals were left for 2 days to ensure sepsis. The infected wounds were treated with topical dressings based on the four groups described above. Wound healing was assessed by daily measurements of the wound length, and complete healing was indicated by complete closure of the wound and growth of hair. Bacterial cultures were done using swabs from wounds to demonstrate the eradication of the *Staphylococcus pyogenes*.

The table below shows that wounds dressed with saline (control group) healed completely after 15.8 days while wounds dressed with acriflavine (1%)-terramycin healed after 10.6 days. Wounds treated with the *Nigella sativa* L. polyunsaturated fatty acid fraction (1% and 5%) dressings showed completed healing after 9.6 and 9.2 days, respectively. Significant differences in the rate of wound healing ($P<0.05$) were observed between control wounds dressed by saline and wounds dressed by either acriflavine-terramycin or *Nigella sativa* L. polyunsaturated fatty acid fraction (1% and 5%). However, no statistical differences in the rate of wound healing were observed between wounds dressed by acriflavine-terramycin and the *Nigella sativa* L. polyunsaturated fatty acid fraction (1 and 5%). Bacterial swabs and cultures confirmed the absence of *Staphylococcus pyogenes* growth.

TABLE 9

| Group | 5 Days | | 7 Days | | 9 Days | | Days for Complete Healing |
|---|---|---|---|---|---|---|---|
| | Wound Length (mm) | Healing Degree (mm) | Wound Length (mm) | Healing Degree (mm) | Wound Length (mm) | Healing Degree (mm) | |
| Control | 4.50 ± 0.20 | 0.40 ± 0.24 | 3.74 ± 0.11 | 1.20 ± 0.20 | 2.00 ± 0.13 | 2.5 ± 0.09 | 14.6 ± 0.50 |
| Acriflavine-Terramycin | 3.18** ± 0.13 | 0.80 ± 0.37 | 2.80** ± 0.25 | 2.40** ± 0.08 | 0.90** ± 0.08 | 3.20** ± 0.24 | 10.6 ± 0.37** |
| *Nigella sativa* L. polyunsaturated fatty acid fraction (1%) | 2.68** ± 0.25 | 1.20 ± 0.17 | 1.94** ± 0.54 | 2.60* ± 0.40 | 0.30** ± .002 | 3.60** ± 0.40 | 9.6 ± 0.24** |

TABLE 9-continued

| Group | 5 Days | | 7 Days | | 9 Days | | Days for Complete Healing |
|---|---|---|---|---|---|---|---|
| | Wound Length (mm) | Healing Degree (mm) | Wound Length (mm) | Healing Degree (mm) | Wound Length (mm) | Healing Degree (mm) | |
| Nigella sativa L. polyunsaturated fatty acid fraction (5%) | 1.80** ± 0.32 | 1.80 ± 0.27 | 1.50** ± 0.31 | 3.00** ± 0.00 | 0.10** ± 0.00 | 3.90** ± 0.10 | 9.2 ± 0.20** |

Values are the mean ± S.E. of observations from 5 guinea pigs.
*Statistically significant from the control group (treated with saline) at $P < 0.05$.
**Statistically significant from the control group (treated with saline) at $P < 0.01$.

Example 12

The aim of the study was to determine whether the *Nigella sativa* L. polyunsaturated fatty acid fraction can alleviate pain (local/central).

Rat was selected as an experimental animal model for this study. The rat tail flicks after exposure to thermal energy was the employed technique (Kuzmin et al., 1994). Rats were exposed to thermal energy through the rat tail flicks apparatus for a maximum of 1 minute at a temperature of 85° C. Ten rats, weighing 250-300 grams each, were divided into two groups (5 rats/group); the first served as the control group and the second was treated with the *Nigella sativa* L. polyunsaturated fatty acid fraction.

For the control group, the rat tail was injected 1 cm from the its proximal and subcutaneously with 50 µl of the vehicle (isopropylmyristate) using a 23 G tuberculin needle, while rats in the second group were injected with 50:1 of *Nigella sativa* L. polyunsaturated fatty acid fraction (20%) solubilized in isopropylmyristate. Animals were exposed to thermal energy immediately (0 time) and 10 minutes following the injection of the *Nigella sativa* L. polyunsaturated fatty acid fraction or the control. The time needed for rat tails to flick after exposure to heat was recorded using a stop watch.

TABLE 10

Rat tail flicks (seconds) after s.c. injection of the *Nigella sativa* L. polyunsaturated fatty acid fraction or its vehicle (n = 5/group).

| Time (min) after injection | Vehicle | *Nigella sativa* L. Polyunsaturated fatty acid fraction |
|---|---|---|
| 0 minutes | 13.9 ± 5.6 | 12.8 ± 2.5 |
| 10 minutes | 14.5 ± 3.5 | 28.1 ± 7.2* |

*Statistically significant from the control rats (injected with isopropylmerestate) at $P < 0.05$.
Values are the mean ± S.D. of observations from 5 rats.

The analgesic activity of the *Nigella sativa* L. polyunsaturated fatty acid fraction was studied using the writhing method described by Okun et al. (1963). Thirty mature mice of both sexes weighing from 20 to 25 gm were divided into 3 groups of 10 mice each. The first group served as a control and the second group served as a standard (treated with paracetamol in a dose of 5 mg/100 gm body weight). The third group was injected subcutaneously with the *Nigella sativa* L. polyunsaturated fatty acid fraction. After 30 minutes, mice were injected intraperitoneally with 0.25 ml of a solution of parabenziquinone (0.2 mg/ml in saline). Mice were observed for writhing every 30 minutes for 2 hours.

Animals devoid of writhing in each group were recorded and the analgesic potencies of paracetamol and the *Nigella sativa* L. polyunsaturated fatty acid fraction were determined as percent protection against writhing.

The analgesic effects of paracetamol and the *Nigella sativa* L. polyunsaturated fatty acid fraction are shown in Table 11. The analgesic property of the *Nigella sativa* L. polyunsaturated fatty acid fraction protected the mice against writhing induced by parabenzoquinone. Protection ranged from 80% to 20% measured 30 minutes to 2 hours following s.c. injection of the *Nigella sativa* L. polyunsaturated fatty acid fraction. Such protection was comparable to that elicited by the use of paracetamol.

TABLE 11

Analgesic effect of the *Nigella sativa* L. polyunsaturated fatty acid fraction in mice using the writhing method (n = 10/group).

| Substance | Dose mg/100 g.b.w. | % Protection (minutes) | | | |
|---|---|---|---|---|---|
| | | 30 | 60 | 90 | 120 |
| Control | | 0 | 0 | 0 | 0 |
| Paracetamol | 5.0 | 100 | 60 | 40 | 20 |
| Test Fraction | 125 | 80 | 60 | 40 | 20 |

Data are the mean of observations from 10 mice/group.

Example 13

Anti-Inflammatory Effect of the *Nigella sativa* L. Polyunsaturated Fatty Acid Fraction The anti-inflammatory activity of the *Nigella sativa* L. polyunsaturated fatty acid fraction was carried out in rats using a modification of rat paw formalin edema as described by Domemjoz et al. (1965).

Fifteen mature albino rats of both sexes weighing 150-200 gm were divided into 3 groups of 5 rats each. At the beginning of the experiment, the thickness of the rat left hind paw was measured using a Vernier caliper. Thereafter, rats of the first group were kept as a control and those of the second group (standard) were injected intraperitoneally with phenylbutazone in a dose of 3 mg/100 gm body weight. Rats of the third group were injected with the *Nigella sativa* L. polyunsaturated fatty acid fraction. After 30 minutes, inflammation was induced by subcutaneous injection of 0.1 mL of 6% solution of formalin in normal saline into the left hind paw.

The anti-inflammatory effect of the *Nigella sativa* L. polyunsaturated fatty acid fraction was estimated by comparing the magnitude of the paw swelling in the pretreated animals with that of the control animals. Measurement of rat paw thickness was carried out at hourly intervals for a period of 3 hours.

The anti-inflammatory effect of the *Nigella sativa* L. polyunsaturated fatty acid fraction is shown in Table 12. The *Nigella sativa* L. polyunsaturated fatty acid fraction produced a statistically significant anti-inflammatory effect compared to the control group. The magnitude of such effect was statistically different from that produced by phenyl butazone.

TABLE 12

Anti-inflammatory effect of phenylbutazone and the *Nigella sativa* L. polyunsaturated fatty acid fraction in rats (n = 5/group).

| Substance | Dose (mg/100 g.b.w.) | Rat Paw Thickness (mm) | | |
|---|---|---|---|---|
| | | 1 Hour | 2 Hours | 3 Hours |
| Control | 0 | 7.24 ± 0.11 | 7.68 ± 0.22 | 7.50 ± 0.44 |
| Phenylbutazone | 3 | 5.85 ± 0.15*** | 5.71 ± 0.09*** | 5.82 ± 0.05*** |
| *Nigella sativa* L. polyunsaturated fatty acid fraction | 125 | 6.46 ± 0.21** | 6.18 ± 0.31** | 6.14 ± 0.24** |

Data are the mean ± S.E. of observations from 5 rats.
**Significant at $P < 0.01$.
***Significant at $P < 0.001$.

Example 14

Chronic Toxicity and Teratogenic Studies of the *Nigella sativa* L. Polyunsaturated Fatty Acid Fraction This study was performed in 2 equal groups, each of 5 weaned male rats of about 55-80 grams body weight and 10 weeks old. The first group served as a control.

For revealing the changes in the activity of some serum enzymes after prolonged administration of the *Nigella sativa* L. polyunsaturated fatty acid fraction, rats were bled to obtain 4 ml blood samples from each rat in a clean dry centrifuge tube. Samples were left to clot and let to stand at room temperature for 20 minutes, then centrifuged at 1500 rpm. The obtained serum was collected and used for the following studies: (1) Determination of the activity of Serum Glutamic-Oxaloacetic Transaminase (SGOT). The activity of SGOT enzyme was measured by Schmidt (1963) modification of Reitman and Frankel (1957) method. (2) Determination of the activity of Serum Glutamic-Pyruvic Transaminase (SGPT). The activity of SGPT enzyme was measured by the method described by Reitman and Frankel (1957). (3) Determination of the activity of serum alkaline phosphatase. The activity of serum alkaline phosphatase was measured according to the method described by Wootton (1954). (4) Determination of blood urea and creatinine. It was done spectrophotometrically. Results were statistically analyzed as explained by Snedecor (1969).

Oral administration of the *Nigella sativa* L. polyunsaturated fatty acid fraction for 12 weeks significantly decreased body weight gain of rats as compared to the control group (Table 13).

Oral administration of the *Nigella sativa* L. polyunsaturated fatty acid fraction for 12 weeks decreased erythrocytic count, packed cell volume and hemoglobin percentage (Table 14). Such decrease in these parameters is still considered in the normal range.

Oral administration of the *Nigella sativa* L. polyunsaturated fatty acid fraction for 12 weeks increased the activity of alkaline phosphatase enzyme (Table 15). It also increased the blood levels of creatinine (Table 15).

At the end of 12 weeks of prolonged administration of the *Nigella sativa* L. polyunsaturated fatty acid fraction, there were no peculiar histopathological changes in hepatic, renal or splenic cells.

Massive doses of the *Nigella sativa* L. polyunsaturated fatty acid fraction amounting to 125 mg/100 grams of rats' body weight administered orally every day for 12 weeks have shown a potential toxicity in the form of decreased body weight gain, increased activity of serum alkaline phosphatase, increased blood creatinine concentration in addition to alterations in some hematological criteria (but still within normal range).

The calculated equivalent dose of such massive dose for human subjects which could be considered to produce similar side effects is about 50 grams given orally every day for 12 weeks. Thus, the compounds and compositions of the present invention can be used for promoting weight loss and/or treating obesity in a patient in need thereof.

One has to consider the therapeutic dose of the composition in Example 4 (20% ointment), which is 1 gram twice daily locally in patients with anal fissures amounting to 0.4 grams of the *Nigella sativa* L. polyunsaturated fatty acid fraction daily for two weeks, is far beyond the calculated toxic dose. On the other hand, not more than 5% of this locally administered dose (0.4 grams of the *Nigella sativa* L. polyunsaturated fatty acid fraction daily) is expected, on the best conditions, to be absorbed systemically from the site of application.

TABLE 13

| | 2 weeks | 4 weeks | 6 weeks | 8 weeks | 10 weeks | 12 weeks |
|---|---|---|---|---|---|---|
| Control | 11.0 ± 0.45 | 29.8 ± 0.80 | 54.2 ± 1.39 | 78.8 ± 1.22 | 93.2 ± 1.24 | 115.0 ± 3.54 |
| *Nigella sativa* L. polyunsaturated fatty acid fraction | 10.4 ± 0.40 | 26.0** ± 1.00 | 37.0** ± 1.22 | 54.2** ± 1.87 | 64.8** ± 1.00 | 76.8** ± 1.20 |

Values are the mean + S.E. of the difference in change of body weight gain of 5 rats from the control group and the *Nigella sativa* L. polyunsaturated fatty acid fraction treated group.
**Significant at $P < 0.01$

TABLE 14

|  | Hb (%) | RBCs ($10^6$/mL) | WBCs ($10^3$/mL) | PCV (%) |
| --- | --- | --- | --- | --- |
| Control | 15.55 ± 0.08 | 6.87 ± 0.05 | 15.20 ± 0.18 | 42.20 ± 1.06 |
| Nigella sativa L. polyunsaturated fatty acid fraction | 14.14* ± 0.20 | 6.59** ± 0.06 | 15.69 ± 0.15 | 39.00* ± 0.72 |

Values are the mean ± S.E. of observations form 5 rats.
*Significant at P < 0.05
**Significant at P < 0.01.

TABLE 15

|  | SGOT (units/mL) | SGPT (units/mL) | Al. Ph. (K.A. units/mL) | Urea (mmol/L) | Creatinine (mg %) |
| --- | --- | --- | --- | --- | --- |
| Control | 42.00 ± 1.22 | 34.80 ± 0.20 | 18.71 ± 0.09 | 38.82 ± 1.81 | 1.47 ± 0.06 |
| Nigella sativa L. polyunsaturated fatty acid fraction | 43.00 ± 1.24 | 33.40 ± 1.03 | 38.05** ± 1.03 | 43.53 ± 2.74 | 2.05** ± 0.19 |

Values are the mean ± S.E. of observations form 5 rats.
**Significant at P < 0.01.

Also in this experiment, 15 pregnant female rats (250-300 grams) were isolated and divided into 3 groups (five rats each). The first group served as a control and was orally administered the same volume of normal saline solution (0.9% NaCl). The second and third groups were orally administered 50 and 150 mg/kg body weight from the *Nigella sativa* L. polyunsaturated fatty acid fraction. Animals were treated according to the previous protocol daily for 10 days (from the sixth day of pregnancy till the fifteenth day). On day 20 of pregnancy, rats were sacrificed and the uteri were inspected and numbers of embryos recorded. Two thirds of the embryos were taken and kept in Boan's solution for examination for possible teratogenic effects. No teratogenic effect was observed both externally or internally in the organs or the vertebral column of the embryos.

In summary, the experimental studies described above demonstrated a significant acceleration of wound healing when using dressings containing the *Nigella sativa* L. polyunsaturated fatty acid fraction in two concentrations. This fraction exhibited analgesic properties as elicited by rat tail flick and writhing methods. Furthermore, in vitro antimicrobial studies of the fraction proved antibacterial actions against common gram positive and gram negative bacteria. Additionally, the *Nigella sativa* L. polyunsaturated fatty acid fraction had anti-allergic effects as proved by protection from histamine-induced bronchospasm in guinea pigs.

Example 15

Phase I Clinical Trials

Six healthy subjects not suffering from diseases were selected from outpatient clinics of some hospitals in Cairo, Egypt. Subjects were screened according to: their medical history (including concomitant medication history); a physical examination and laboratory investigations (e.g. chest X ray, ECG, liver and kidney function tests, urine for glucosuria); and an anal examination.

Healthy subjects (free from anal abnormalities and pathologies) of both sexes with age ranging from 25 to 35 years were enrolled in the study. Those patients with anal abnormalities and pathologies, diabetes and neurological disorders, emotional or psychological instability, or those taking steroid medications or smooth muscle relaxants were excluded from the study.

Healthy subjects willing to participate in phase I clinical trial had a complete physical and surgical examination in addition to laboratory investigations. Subjects were asked to apply the ointment in Example 4 (twice daily for two weeks) in the anal canal. They were hospitalized for 48 hours where all vital signs were monitored and laboratory investigations (including liver and kidney function tests, hematological studies, urine and stool analyses in addition to an ECG and chest X-ray) were done immediately before and by the end of the period of administration of the ointment of Example 4. Patients were allowed to attend the outpatient clinic of the hospital twice weekly for check ups. On the 14th day, they were readmitted for clinical and laboratory evaluation. Prior to the trial, a signed consent was obtained from the volunteers.

No local irritation or sensitization was observed in the subjects. Physical examination and laboratory investigations carried out at the end of the second week revealed no statistically different changes.

The phase I clinical trial demonstrated that applying the ointment of Example 4 daily for 14 days is quite safe and well tolerated without the incidence of any observable local or systemic side effects, side reactions or toxicity in all subjects enrolled in the trial.

Example 16

Phase II Clinical Trials

Patients suffering from acute and chronic anal fissures were selected from outpatient clinics of some hospitals. All subjects were screened according to their medical history (including concomitant medication history); a physical examination and laboratory investigations (e.g. urine for glucousuria); and an anal manometry was done for cases of anal fissure to assess the need for surgical interference. Normal (resting) anal pressure is 10-30 mmHg and the maximum normal anal pressure is 60-110 mmHg.

Patients having anal fissures were treated with a topical composition comprising the *Nigella sativa* L. polyunsaturated fatty acid fraction of the present invention by topically applying 2 grams of the ointment twice daily for two weeks. Relief started immediately and gradual healing began after 3 days.

As shown in table 16, phase II clinical studies demonstrated that the ointment of Example 4 was effective in the treatment of acute and chronic anal fissure. The ointment of Example 4 achieved a 100% success in the treatment of acute anal fissure (70% total cure and 30% improvement); and achieved an 89% success in the treatment of non-surgical cases of chronic anal fissure (58% total cure and 31% improvement). The ointment of Example 4 was, therefore, considered superior to conventional drugs utilized in the treatment of acute and chronic anal fissures.

TABLE 16

| Disease | # of Cases | Results | # of Cases | % | Evaluation* | |
|---|---|---|---|---|---|---|
| Acute Anal Fissure | 20 | Total Cure | 14 | 70 | Better | + |
|  |  | Improvement | 6 | 30 | Equal |  |
|  |  | Limited | — |  | Less |  |
| Chronic Anal Fissure | 26 | Total Cure | 15 | 58 | Better | + |
|  |  | Improvement | 8 | 31 | Equal |  |
|  |  | Limited | 3 | 11 | Less |  |

*Evaluation of the response to the ointment in Example 4 was done by comparing relief of symptoms and healing of the anal fissure produced by the ointment in Example 4 to that produced by the use of a conventional drug therapy (# of patients was 10 in the control group).

Total cure was a disappearance of symptoms with complete healing of the fissure. Improvement was a disappearance of symptoms with the presence of the fissure. Limited response was a decrease in symptoms with the presence of the fissure (limited improvement).

The ointment of Example 4 possesses local antiseptic and antibacterial effects, wound healing promoting properties in addition to analgesic actions. Phases I and II clinical trials indicate that the use of the ointment in Example 4 is superior in the treatment of acute and non-surgical cases of chronic anal fissure and that it is a potent and safe formula that can be used successfully in the treatment of anal fissures.

Example 17

This example explains in vivo studies to evaluate the prophylactic (protective) anti-asthmatic effect of the *Nigella sativa* L. polyunsaturated fatty acid fraction. The prophylactic antiasthmatic effect was evaluated in vivo by measurement of the preconvulsive time in guinea pigs exposed to histamine aerosol (0.25%).

Guinea pigs were divided into three groups with 8 animals per group. The first group received a saline injection to serve as negative control. The second group received ketotifen, which is the standard treatment to serve as positive control. The third group received 200 mg/kg of the *Nigella sativa* L. polyunsaturated fatty acid fraction.

Animals in all groups were treated for 21 days, after which they were exposed to histamine (0.25%) aerosol and the preconvulsive time was recorded. The results are shown in table 17 below.

TABLE 17

| Treatment | Preconvulsive time mean ± SD (seconds) | % of Prophylaxis (Protection) | Dosage |
|---|---|---|---|
| saline - negative control | 71.6 ± 14.6 | 11.9 |  |
| ketotifen positive standard | 497.1* ± 183.2 | 82.85 | 5 microg/kg |
| *Nigella sativa* L. polyunsaturated fatty acid fraction | 118 ± 39.5 | 19.7 | 200 mg/kg |

*Statistically significant from the control group (P < 0.05).

Example 18

This example explains an in vivo study to evaluate the tachypnea (protective) effect of the *Nigella sativa* L. polyunsaturated fatty acid fraction.

The second protocol involved sensitized animals. Animals were sensitized by injecting ova albumin in two doses 100 mg. each (S.C. and I.P., simultaneously). Animals were resensitized 15 days later. Guinea pigs were divided into three groups with 8 animals per group. The first group received a saline injection to serve as negative control. The second group received ketotifen which is the standard treatment to serve as positive control. The third group received 200 mg/kg each of *Nigella sativa* L. polyunsaturated fatty acid fraction.

Animals in all groups were treated for 21 days following which they were exposed to ova albumin inhalation and time to onset of tachypnea was recorded as shown in the table below (* Statistically significant from the control group (P<0.05)).

TABLE 18

| Treatment | Time to attain Tachypnea mean ± SD (seconds) | % of Prophylaxis | Dosage |
|---|---|---|---|
| saline - negative control | 81.4 ± 33.3 | 13.6 |  |
| ketotifen positive standard | 266.3* ± 128 | 44.4 | 50 microg/kg |
| *Nigella sativa* L. polyunsaturated fatty acid fraction | 154.3* ± 44.8 | 25.7 | 200 mg/kg |

All publications, including, but not limited to, patents and patent applications cited in this specification, are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration it is believed that one skilled in the pharmaceutical art can, given the preceding description, utilize the present invention to its fullest extent, using no more than routine experimentation. Therefore any examples are to be construed as merely illustrative and not a limitation on the scope of the present invention in any way. Accordingly, it will be apparent to one skilled in the art that various modifications can be made to the invention without departing from the spirit or scope of the appended claims.

What is claimed is:

1. A method of treating a skin condition arising from fungal infection, bacterial infection, allergic reaction, or inflammation in a patient in need thereof comprising the step of topically administering an effective amount of a semi-solid composition formulated for topical administration, said composition consisting essentially of a purified polyunsaturated fatty acid fraction extracted from *Nigella sativa* L. seeds and a pharmaceutically acceptable carrier, wherein said polyunsaturated fatty acid fraction consists of polyunsaturated fatty acids and is free of *Nigella sativa* L. saturated fatty acids, sterols, volatile oils, and glyceryl esters.

2. The method of claim 1, wherein the semi-solid composition has skin moisturizing, revitalizing, and analgesic effects.

3. The method of claim 1, wherein the skin condition is selected from the group consisting of psoriasis, eczema, dermatitis, dry, scaly, itchy or flaky skin, diaper rash, athlete's foot, jock itch, scalp irritations, and dermal infections.

4. The method of claim 1, wherein the polyunsaturated fatty acid fraction is present in an amount ranging from about 15 to about 28% by weight based on 100 parts by weight of the total composition.

5. The method of claim 1, wherein the polyunsaturated fatty acid fraction is present in an amount ranging from about 18 to about 25% by weight based on 100 parts by weight of the total composition.

6. The method of claim 1, wherein the polyunsaturated fatty acid fraction is present in an amount ranging from about 20 to about 23% by weight based on 100 parts by weight of the total composition.

7. The method of claim 1, wherein the composition further comprises at least one compound selected from the group consisting of an emulsifying agent, a stabilizing agent and a preservative.

8. The method of claim 1, wherein the semi-solid composition contains from about 1 to about 33% by weight polyunsaturated fatty acid fraction, based on 100% by weight of the total composition.

9. The method of claim 1, wherein the polyunsaturated fatty acid fraction consists essentially of octadecadienoic acid and octadecenoic acid.

10. The methods of claim 9, wherein the octadecadienoic acid is present in the polyunsaturated fatty acid fraction in an amount ranging from about 60.7 to about 72.6% by weight, and the octadecenoic acid is present in the polyunsaturated fatty acid fraction in an amount ranging from about 23.8 to about 29.7% by weight.

* * * * *